(12) United States Patent
Renshaw et al.

(10) Patent No.: US 9,146,205 B2
(45) Date of Patent: Sep. 29, 2015

(54) VIBROTHERMOGRAPHIC WELD INSPECTIONS

(75) Inventors: Jeremy B. Renshaw, Concord, NC (US); Samuel W. Glass, III, Lynchburg, VA (US); Bradley A. Thigpen, Harrisburg, NC (US); Matthieu Taglione, Dijon (FR)

(73) Assignee: AREVA Inc., Lynchburg, VA (US)

( * ) Notice: Subject to any disclaimer, the term of this patent is extended or adjusted under 35 U.S.C. 154(b) by 677 days.

(21) Appl. No.: 13/465,316

(22) Filed: May 7, 2012

(65) Prior Publication Data

US 2012/0288049 A1 Nov. 15, 2012

Related U.S. Application Data (60) Provisional application No. 61/484,319, filed on May 10, 2011.

(51) Int. Cl.
| | | |
|---|---|---|
| *G21C 17/00* | (2006.01) | |
| *G01N 25/72* | (2006.01) | |
| *G21C 17/01* | (2006.01) | |
| *G21C 17/017* | (2006.01) | |

(52) U.S. Cl.
CPC ............... *G01N 25/72* (2013.01); *G21C 17/01* (2013.01); *G21C 17/017* (2013.01)

(58) Field of Classification Search
CPC ....... G21C 17/01; G21C 17/017; G01N 25/72
See application file for complete search history.

(56) References Cited

U.S. PATENT DOCUMENTS

| | | | |
|---|---|---|---|
| 6,236,049 B1 * | 5/2001 | Thomas et al. ............ | 250/341.6 |
| 6,399,948 B1 * | 6/2002 | Thomas et al. ............ | 250/341.6 |
| 6,730,912 B2 | 5/2004 | Sun et al. | |
| 6,856,662 B2 | 2/2005 | Glass et al. | |
| 6,998,616 B2 * | 2/2006 | Favro et al. ................ | 250/341.6 |
| 7,060,971 B2 * | 6/2006 | Zombo et al. .............. | 250/341.6 |
| 7,312,454 B2 | 12/2007 | Safai et al. | |
| 7,690,257 B2 | 4/2010 | Meier et al. | |
| 2003/0106376 A1 * | 6/2003 | Shirzad et al. .................. | 73/606 |
| 2004/0228432 A1 * | 11/2004 | Glass et al. .................... | 376/249 |
| 2007/0253519 A1 * | 11/2007 | Meier et al. ................... | 376/260 |
| 2010/0011864 A1 | 1/2010 | Hanan et al. | |

OTHER PUBLICATIONS

T. Sakagami et al., "Detection of Stress Corrosion Cracking by Sonic-IR Technique," NDT.net e-Journal (www.ndt.net), Jun. 2010.

M. Piriou et al., "The Photothermal Camera Method Technology Update and Recent Results," NDT.net e-Journal (www.ndt.net), Aug. 2010.

(Continued)

*Primary Examiner* — Jack W Keith
*Assistant Examiner* — Daniel Wasil
(74) *Attorney, Agent, or Firm* — Sean P. O'Hanlon, Esq., PLLC (57) ABSTRACT

The present invention is related to a system and method of inspecting a weld. The weld to be inspected is subjected to a transient sonic excitation while the weld area is monitored using a remote infrared camera. The sonic excitation induces mechanical vibration, which causes heat generation at any cracks or other anomalies in the weld. The infrared camera detects any temperature differentials in the weld, indicating the presence of an anomaly. The system and method is particularly useful for welds in environments that are unsafe for extended human presence or that are crowded or otherwise inaccessible, such as with piping or other structural components.

16 Claims, 4 Drawing Sheets

(56) References Cited

OTHER PUBLICATIONS

W. T. Kim et al., "Detection of Piping Defects in Nuclear Plants by Ultrasonic Pulse-Phase Thermography," NDT.net e-Journal (www.ndt.net), Aug. 2010.

J. Dimambro et al., "Sonic Infrared (IR) Imaging and Fluorescent Penetrant Inspection Probability of Detection (POD) Comparison," American Institute of Physics, AIP Conf. Proc. 894, pp. 463-470, 2006.

* cited by examiner

VIBROTHERMOGRAPHIC WELD INSPECTIONS

CROSS-REFERENCE TO RELATED APPLICATIONS

This patent application claims the benefit of U.S. Provisional Patent Application No. 61/484,319 filed on May 10, 2011, which is incorporated herein by reference in its entirety.

BACKGROUND OF THE INVENTION

1. Field of the Invention

The present invention relates to the inspection of welds using vibrothermography, and, more particularly, the present invention relates to inspecting and determining the quality of J-groove welds of a nuclear reactor pressure vessel (RPV) head and the RPV bottom mounted nozzles (BMNs) using vibrothermography.

2. Description of the Related Art

Nuclear reactors have a reactor cover or closure head through which a series of openings having tubes extending therethrough to the inside surface of the reactor are welded to the closure head by J-groove welds. These tubes have control rod drives and instrumentation packages sealably extending into the reactor internals. Similarly, the bottom portion of the RPV contains penetrations with instrumentation packages that are also connected to the RPV via J-groove welds.

Certain parts of the reactor vessel head are known to be susceptible to stress corrosion cracking. Many reactor heads have been completely replaced well before the planned design life because of extensive cracking in the nozzles and/or J-groove welds. The J-groove welds must be inspected during reactor shut down for any cracks that may have developed in the welds. Such inspections are usually made from beneath the reactor head with the head on a supporting headstand during normal refueling periods. J-groove welds are difficult to inspect due to the complex geometry and high radiation fields under the head. Visual techniques are known to have difficulty with very small, tight surface cracks, especially on rough surfaces or after certain processes (i.e., grinding are used to improve surface finish for inspection. Standard nondestructive examination techniques such as eddy current and dye-penetrant examinations are the typical inspection approach used; however, application of these techniques is time-consuming in an operational environment where delays associated with inspections are undesirable. If ultrasound techniques are used for an RPV head inspection, the water couplant must be managed and disposed of following the inspection. Dye-penetrant techniques also suffer from disadvantages including requirements for cleaning the surface, a process that can involve significant volumes of solvent and chemicals.

High radiation under the reactor head makes it undesirable for personnel to perform these inspections by direct contact with the components; thus, various robotic elements are used to remotely access these welds with the mentioned nondestructive testing machinery. The robotic challenges with these techniques are significant, typically requiring a close proximity or actual contact to the tested weld surface which is difficult to achieve with the robotic delivery devices and the remotely controlled tools used to access the welds.

Thus, some form of nondestructive remote inspection of J-groove welds that did not require close proximity or contact with the welded surface, nor the exact robotic manipulation associated therewith (which is difficult to implement), was needed. One such form of testing is described in U.S. Pat. No. 6,856,662, the disclosure of which is incorporated herein by reference. This patent describes a photothermal inspection method, which includes sequentially heating small areas of a weld using a laser while monitoring the weld area using a remote infrared camera. The laser and camera are positioned at an angle of approximately 45° to the inspection surface normal. At cracks or other anomalies (referred to herein collectively as cracks), the thermal wave imparted by the laser does not propagate as rapidly, thereby producing an indication of the crack as a sharp drop in the thermal scan at the point of the crack. The temperature differential is detected using the infrared camera.

While the photothermal inspection method of the '662 patent is an improvement over prior J-groove weld inspection methods, it is desirable to use a nondestructive inspection system and method that allows for a quicker inspection.

SUMMARY OF THE INVENTION

The present invention is related to a system and method of inspecting the J-groove welds of a nuclear reactor vessel head or BMN using vibrothermography. The weld to be inspected is subjected to a transient sonic excitation while the weld area is monitored using a remote infrared camera. The sonic excitation induces mechanical vibration, which causes heat generation at any cracks in the weld. The infrared camera detects any temperature differentials in the weld, indicating the presence of a crack. For underwater examinations, as in the case of a BMN, a cofferdam may be used to purge the water surrounding the J-groove weld to make the inspection process possible.

This vibrothermographic inspection is quicker than photothermal inspection. The vibrothermography system and method utilizes much larger inspection areas, eliminating the need to work incrementally with small inspection areas. Vibrothermographic inspection is a form of active thermography wherein the applied external stimulus causes the defect itself to generate heat. The sonic excitation stimulus of vibrothermographic inspection is effective regardless of the angle of attack to the weld. Likewise, detection of the crack's heat signature is largely independent of the camera angle relative the inspection zone. Thus, the setup for vibrothermographic inspection is easier and quicker. For all of these reasons, vibrothermographic inspection is an improvement over known inspection techniques. Vibrothermography is also not sensitive to the surface roughness of an inspected object (as long as there is a line of sight to the inspected areas) and vibrothermography can deal with complex geometries/surfaces much better than ultrasound or eddy current since the camera is an optical device only requiring line-of-sight access to the target surface.

The method of inspecting a J-groove weld in a nuclear reactor may include providing a vibration device and an imaging device near the weld. The vibration device may make physical contact with the weld to be inspected, but more preferably does not make contact with the weld. The vibration device is used to impart acoustic energy to the weld under inspection, and may impart one or more of a range of frequencies to the weld. The range may extend from near DC frequencies to over 50 kHz, and preferably extends to over 100 kHz. The imparted acoustic energy is chosen so as to generate vibration of the weld and friction at a flaw that may be located within the weld, which friction generates heat. The flaw may be located beneath the surface of the weld, in which case the generated heat may be transferred by conduction to the surface of the weld.

The method further includes obtaining a thermal image of the weld using the imaging device such as an infrared camera. The image(s) captured by the imaging device is processed and analyzed to determine the presence of any heat differential within the image, such as an area of relatively higher temperature caused by vibrational friction at a flaw. The determination can then be made, based on the analysis, whether a flaw within the weld or heat affected zone is present.

The inspection method may be repeated a number of times to inspect multiple J-groove welds within the reactor. As the vibration device need not be in contact with the weld under inspection, and furthermore need not be positioned individually with respect to the weld under inspection, the inspections of multiple J-groove welds could be made without repositioning the vibration device.

The vibration device preferably includes a broadband or single frequency piezoelectric transducer to induce vibration of the weld, the piezoelectric transducer preferably being variable to impart a range of frequencies and vibration amplitudes to the weld. The vibration energy transmitted by the vibration device is chosen so as not to exacerbate any flaw within the weld under inspection or any other welds in the proximity of the inspection system.

The inspection system may further include a manipulator to which the imaging device is coupled, and a communication system operatively linking the vibration device, the imaging device, and the manipulator. The system can thus be remotely controlled to position the camera and/or manipulator as needed to perform inspections. The vibration device may also be coupled to the manipulator, allowing the user to reposition it as needed. The communication system preferably is software-driven, synchronizing the inspection system components.

DESCRIPTION OF THE DRAWINGS

The present invention is described with reference to the accompanying drawings, in which like reference characters reference like elements, and wherein.

DETAILED DESCRIPTION OF THE INVENTION

Vibrothermography, also known as sonic IR and thermosonics, is a nondestructive evaluation technique that uses sonic excitation (vibration) to preferentially heat cracks in metal, ceramics, polymers, and composites. This local temperature change may be detected remotely using an infrared (IR) camera. This phenomenon and general test approach is applied to the reactor vessel head by injecting a transient sonic excitation while monitoring the J-groove weld area with a remote infrared camera. Any cracks that "light-up" can be detected and marked for further characterization and evaluation or repair.

The instant system and inspection method provides advantages over other known vibrothermography or alternative non-destructive examination inspection systems and methods. The inventive technique can be implemented with simple remote tools that do not require complex motions to track the complex weld surface. The crack indication is visually clear and can readily be correlated with the exact position on the structure (unlike, for example, eddy current examination techniques). The camera can be operated and positioned remotely from the weld under inspection, reducing radiation influences on the camera. Unlike penetrant or ultrasonic techniques, there are no chemicals or solvents to manage or dispose of following the procedure. Vibrothermography requires little or no surface cleaning, and can be performed significantly faster than known techniques such as ultrasonic, penetrant, and eddy current examinations. The rate of false calls (a defect is called when none is present) for vibrothermography is lower than with most other nondestructive examination techniques. See, for example, J. DiMambro et al., "Sonic Infrared (IR) Imaging and fluorescent Penetrant Inspection Probability of Detection (POD) Comparison," American institute of Physics, AIP Conf. Proc. 894, pp. 463-470, 2006.

Figure 1:
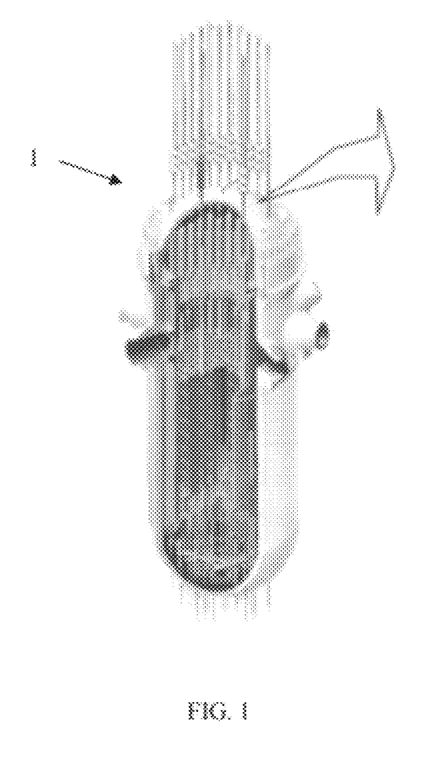
FIG. 1 shows a nuclear reactor vessel in which the inventive system can be used.
Figure 2:
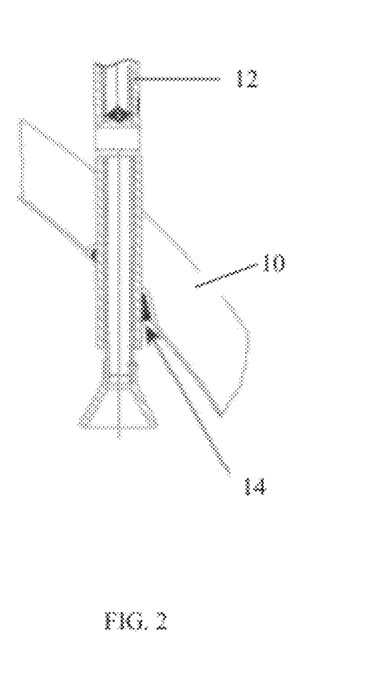
FIG. 2 shows close-up of the nuclear reactor vessel of FIG. 1.

A known nuclear reactor vessel 1 is shown in FIG. 1, and an exemplary head 10, tube 12, and J-groove weld 14 configuration is shown in FIG. 2. The vessel 1 has a series of Inconel 600 control rod drive tubes 12 extending through the dome of the reactor head 10. The carbon steel dome is clad with approximately 0.5 in. of stainless steel. The tubes 12 are welded to the head 10 by a known J-groove weld 14, which must be inspected for flaws during reactor refuel and maintenance outages to ensure the weld integrity remains intact.

Figure 3:
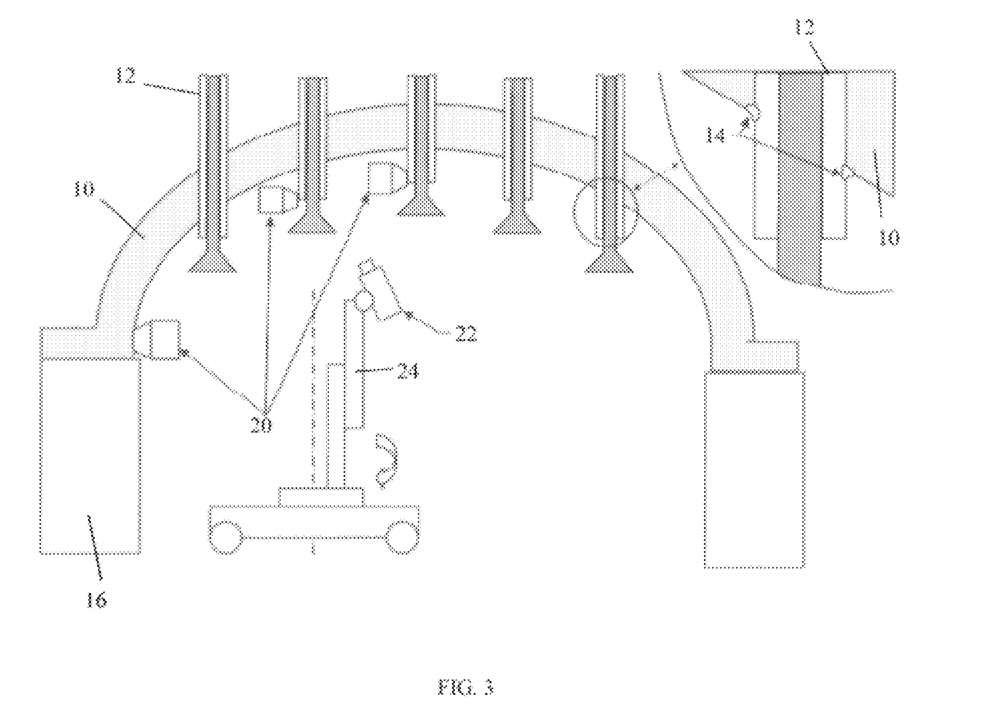
FIG. 3 shows a preferred layout for vibrothermographic inspection system of the present invention.

FIG. 3 shows a preferred layout for vibrothermographic inspection of the J-groove welds 14. The head 10 has been removed from the reactor vessel 1 and placed on a supporting head-stand 16, such as during a normal refueling outage. One or more sonic exciters 20 have been positioned at advantageous positions near the head 10 and/or tubes 12. The exciters 20 can be in contact with the head 10, or tubes 12, and need not be in direct contact with the welds 14. While three such exciters 20 are show in the illustrative embodiment depicted in FIG. 3, more or fewer exciters 20 can be used. Likewise, the exciter locations shown in FIG. 3 are exemplary; other locations could be used as determined by the user for the particular application.

Application of acoustic energy in the instant invention is novel with respect to known vibrothermographic systems. One and often more broadband piezoelectric transducers are preferably used with the instant invention and have been modified to function underwater. The inventive excitation system has significantly improved functionality over the ultrasonic welders, piezoelectric transducers, and variations thereof used in nearly all other vibrothermographic inspections. An important aspect of nondestructive testing is that the testing not create or worsen any existing damage in the equipment being inspected. Typically-used ultrasonic welders have been shown to grow cracks, and thus fail to be nondestructive. Moreover, this crack growth can occur quite rapidly, on the order of 10% to 500% or more growth after approximately 10-15 seconds of excitation. Thus, typical vibrothermographic inspection systems are not appropriate for use in environments where equipment integrity and safety are important, such as a nuclear power plant. The instant excitation system is a lower-power system that does not negatively affect existent cracks. The instant weld inspection system and method is therefore appropriate for use in environments where safety is a primary concern.

The instant excitation system is also variable, providing a wider bandwidth of imparted vibration. Whereas most known systems have a bandwidth of 15-25 kHz or a single frequency at, typically, 20, 30, or 40 kHz, the exciters 20 preferably are broadband transducers capable of generating vibrations over a 50 kHz range of frequencies, and more preferably having a range of 100 kHz or more, from near DC to more than 100 kHz.

Figure 6:
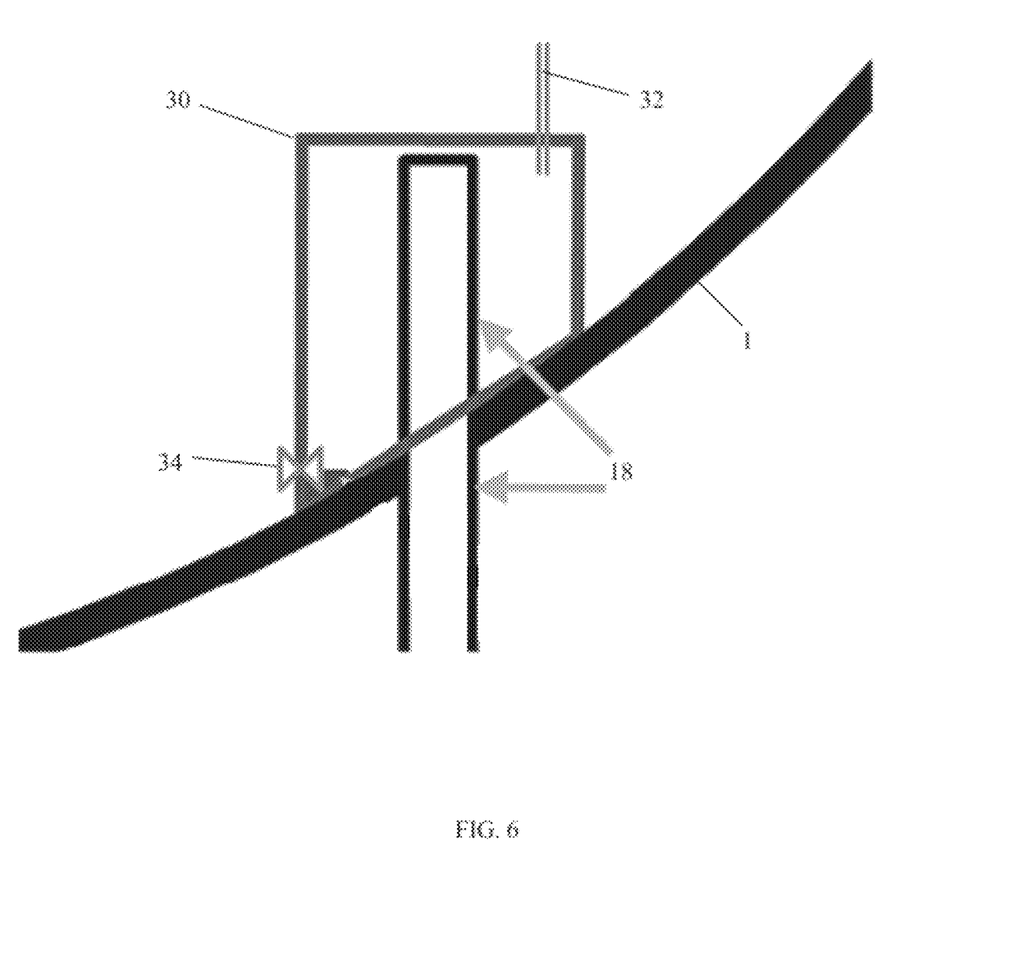
FIG. 6 shows a preferred layout for vibrothermographic inspection system of the present invention in an underwater environment.

The exciters 20 are robust, and have been modified to allow them to function in moist, humid, condensing, or underwater environments. This modification may be achieved, for example, by coating the exciters 20 is an adhesively-bonded polymer coating. Other means of such modification will be apparent to those of skill in the art. Such modification is particularly useful in the inspection of J-groove welds 14 of a nuclear reactor vessel head 10 and allows some inspections to be performed in a noncontact setup by coupling vibrations to the inspected structure through water. This functionality is not present in any other known vibrothermography systems. A cofferdam 30 may be used to purge the water surrounding the J-groove to facilitate the inspection process. FIG. 6 shows a possible layout of for vibrothermographic inspection system of the present invention of a BMN 18. An air hose 32 and valve 34 may be used in conjunction with the cofferdam 30 to replace water within the cofferdam 30 with air. It may not be necessary to remove all of the water from within the cofferdam 30, as shown in the illustrated embodiment of FIG. 6.

Additional benefits of the instant exciters 20 include higher system repeatability and more compact size allowing fur inspections in confined spaces.

In use, the exciters 20 are programmed to impart vibration energy to the tubes 12 and J-groove welds 14. The frequency of the imparted energy is a function of the target components, and includes such considerations as material properties and dimensions of such components. Preferably, a range of frequencies is imparted from the exciters 20 to the tubes 12 and welds 14. The imparted energy causes the target components to vibrate. This vibration causes friction at any crack within the welds 14, which friction generates heat. This localized heat signature is detected by the infrared camera 22, which is positioned to observe one or more of the tubes 12 and welds 14. The instantaneous detection zone of the instant system and method is much larger than with a photothermal inspection method. For example, the detection zone of the instant invention may fully inspect a square foot or larger area in a matter of a few (i.e., less than five) seconds, whereas the detection zone of a photothermal system during the same amount of time may be a ten square inches or less. As the presence of heat indicates the presence of a crack, the instant system and method can detect cracks that are internal to the weld 14 by the heat transfer from the crack outward to the surface of the weld 14.

Figure 4:
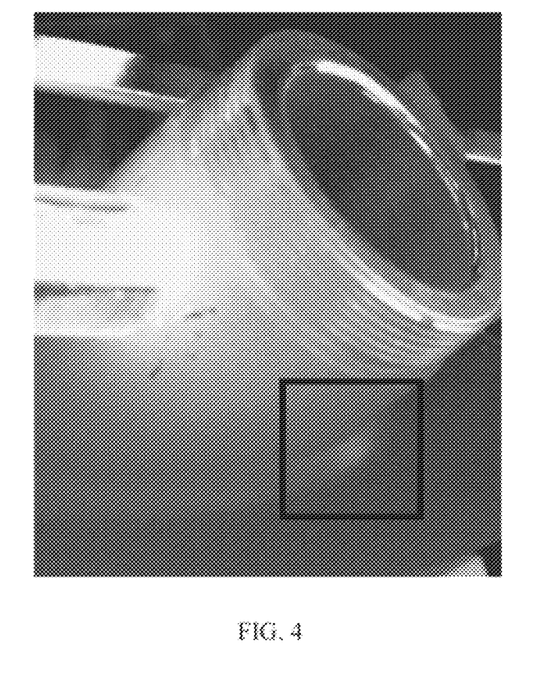
FIG. 4 shows a raw thermal image of a flawed weld sample.
Figure 5:
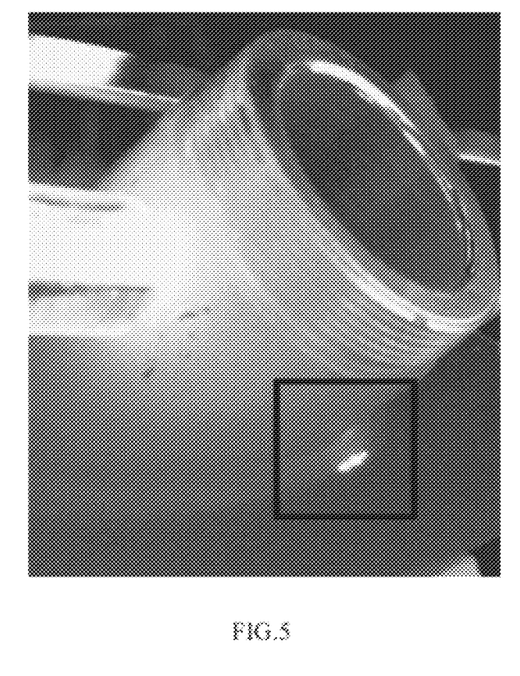
FIG. 5 shows an inspection image of the weld sample of FIG. 4 generated according to the system and method of the instant invention.

FIGS. 4 and 5 illustrate an example measurement. FIG. 4 shows a raw thermal image of a flawed weld sample. While not seen in this figure, the location of a bad weld is highlighted. by the box. An image of the same weld sample after being subjected to vibration from an exciter 20 is shown in FIG. 5. This crack is readily detected by its generated thermal signature and associated image processing.

The camera is coupled to a robotic manipulator 24 that is used to position the camera 22 as needed to make inspections of the various J-groove welds 14. As the exciters 20 do not have to be repositioned for the inspection of each weld 14, the exciters 20 do not have to be coupled to the manipulator 24. The user may choose to couple one or more exciters 20 to the manipulator 24, however, which may eliminate the need for a separate step of positioning the exciters 20 within the head 10.

In some instances, it may be possible to detect the thermal signatures of many cracks from a significant distance, such as from outside the refueling pool in which the head 10 is positioned during a refueling outage. In such an instance, it may be possible for a person to manually handle the camera safely, foregoing the need to use the robotic manipulator 24, at least for inspection of the upper portion of the welds 14 (near the outer surface of the head 10).

Each of the exciter 20, camera 22, and manipulator 24 (if used) preferably is remotely controlled. Preferably, each of these components is controlled by software that is either fully automated or user-driven. The control system allows for individual or multiple exciters 20 to be used, and for single frequency, multiple simultaneous frequencies, and/or frequency sweep excitation modes to be used. If multiple exciters 20 are used, they may be programmed to use the same or different frequencies or frequency ranges. The control system can also process the image data captured by the camera 22 to pick out important information from each test. This software can be expanded as necessary to incorporate changing technical requirements.

While the preferred embodiments of the present invention have been described above, it should be understood that they have been presented by way of example only, and not of limitation. It will be apparent to persons skilled in the relevant art that various changes in form and detail can be made therein without departing from the spirit and scope of the invention. Thus the present invention should not be limited by the above-described exemplary embodiments, but should be defined only in accordance with the following claims and their equivalents. Furthermore, while certain advantages of the invention have been described herein, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

What is claimed is:

1. A method of inspecting a J-groove weld in a nuclear reactor, comprising:
    providing an electrically operated vibration device near the weld;
    providing an electrically operated thermal imaging device near the weld;
    vibrating the weld with said vibration device;
    obtaining a thermal image of the weld with said imaging device;
    analyzing said thermal image; and
    determining, based on said analyzing, whether there is a flaw within the weld;
    wherein said providing said vibration device includes positioning said vibration device in a position such that it is not in physical contact with the weld; and
    wherein said vibration the weld includes operating said vibration device while said vibration device is in said position.

2. The method of claim 1, wherein said vibrating includes imparting acoustic energy to said weld.

3. The method of claim 2, wherein said imparting includes imparting a single frequency, multiple simultaneous frequencies, or a range of frequencies to the weld.

4. The method of claim 3, wherein said imparting further includes imparting a 100 kHz range of frequencies to the weld.

5. The method of claim 2, wherein said imparting includes generating friction at a flaw located within the weld.

6. The method of claim 5, wherein said imparting includes generating friction at a flaw located beneath a surface of the weld.

7. The method of claim 5, wherein said obtaining includes obtaining an image of heat generated by said friction.

8. The method of claim 7, wherein said obtaining includes obtaining an image of heat generated beneath a surface of the weld and transferred to the surface of the weld.

9. The method of claim 7, wherein said analyzing includes determining the presence of any heat differential within said image.

10. The method of claim 9, wherein said analyzing includes determining the presence of an area of relatively high temperature.

11. The method of claim 9, wherein said determining includes determining whether any heat differential in said image results from a flaw within the weld.

12. A method of inspecting a plurality of J-groove welds in a nuclear reactor, comprising:
providing a vibration device near the plurality of J-groove welds;
providing an imaging device near a selected one of the plurality of J-groove welds;
vibrating the plurality of J-groove welds with said vibration device;
obtaining a thermal image of the selected one of the plurality of J-groove welds with said imaging device;
analyzing said thermal image; and
determining, based on said analyzing, whether there is a flaw within the selected one of the plurality of J-groove welds; and
making a plurality of iterations of inspections for others of the plurality of J-groove welds within the reactor;
wherein inspections of multiple J-groove welds are made without repositioning said vibration device.

13. A method of inspecting a J-groove weld between a tube and a nuclear reactor pressure vessel, comprising:
providing a vibration device near the tube or the pressure vessel;
providing a thermal imaging device near the weld;
imparting a transient sonic excitation to the weld with said vibration device;
obtaining a thermal image of the weld with said imaging device;
analyzing said thermal image to identify the presence of any heat differential within the weld; and
determining, based on said analyzing, whether there is a flaw within the weld;
wherein said providing said vibration device includes positioning said vibration device in a position such that it is not in physical contact with the weld; and
wherein said imparting the transient sonic excitation to the weld includes operating said vibration device while said vibration device is in said position.

14. The method of claim 13, wherein said providing said vibration device includes providing said vibration device in the form of a sonic exciter.

15. The method of claim 13, wherein:
said imparting includes generating friction at a flaw located within the weld;
said obtaining includes obtaining an image of heat generated by said friction;
said analyzing includes determining the presence of any heat differential within said image; and
said determining includes determining whether any heat differential in said image results from a flaw within the weld.

16. The method of claim 13, including making a plurality of iterations of inspections for a plurality of J-groove welds within the pressure vessel, wherein inspections of multiple J-groove welds are made without repositioning said vibration device.

* * * * *

UNITED STATES PATENT AND TRADEMARK OFFICE
CERTIFICATE OF CORRECTION

| | | |
|---|---|---|
| PATENT NO. | : 9,146,205 B2 | Page 1 of 1 |
| APPLICATION NO. | : 13/465316 | |
| DATED | : September 29, 2015 | |
| INVENTOR(S) | : Jeremy B. Renshaw et al. | |

It is certified that error appears in the above-identified patent and that said Letters Patent is hereby corrected as shown below:

Claims

Column 6, line 57, in claim 1, line 16, "vibration" should be changed to -- vibrating --.

Signed and Sealed this
Fifteenth Day of March, 2016

Michelle K. Lee
*Director of the United States Patent and Trademark Office*